US009771668B2

(12) United States Patent
Montenegro et al.

(10) Patent No.: US 9,771,668 B2
(45) Date of Patent: Sep. 26, 2017

(54) CHITOSAN FIBER

(75) Inventors: Rivelino Montenegro, Mainz (DE); Thomas Freier, Mainz (DE)

(73) Assignee: Medovent GmbH, Mainz (DE)

( * ) Notice: Subject to any disclaimer, the term of this patent is extended or adjusted under 35 U.S.C. 154(b) by 1056 days.

(21) Appl. No.: 13/576,327

(22) PCT Filed: Feb. 2, 2010

(86) PCT No.: PCT/EP2010/051231
§ 371 (c)(1),
(2), (4) Date: Oct. 22, 2012

(87) PCT Pub. No.: WO2011/095203
PCT Pub. Date: Aug. 11, 2011

(65) Prior Publication Data
US 2013/0041407 A1    Feb. 14, 2013

(51) Int. Cl.
*D01F 9/00* (2006.01)
*A61L 17/08* (2006.01)
*D06M 13/188* (2006.01)

(52) U.S. Cl.
CPC .............. *D01F 9/00* (2013.01); *A61L 17/08* (2013.01); *D06M 13/188* (2013.01); *Y10T 428/298* (2015.01)

(58) Field of Classification Search
CPC ....................................................... A61L 17/08
USPC ............................................................ 606/231
See application file for complete search history.

(56) References Cited

U.S. PATENT DOCUMENTS 5,897,821 A        4/1999   Kawasaki
2008/0254125 A1*   10/2008  Freier ........................... 424/488

FOREIGN PATENT DOCUMENTS

WO    WO-2009097545 A1    8/2009

OTHER PUBLICATIONS

International Search Report and Written Opinion of the International Searching Authority for PCT/EP2010/051231 dated Nov. 8, 2010 (19 pages).
Malheiro, V.N. et al., "New poly (ε-caprolactone)/chitosan blend fibers for tissue engineering applications," 2010 Acta Biomaterialia, vol. 6 (pp. 418-428).
Zheng, H. et al., "Preparation and Characterization of Chitosan/Poly(vinyl alcohol) Blend Fibers," 2001 Journal of Applied Polymer Science, vol. 80 (pp. 2558-2565).
Ohkawa, K. et al., "Preparing Chitosan-Poly(acrylic Acid) Composite Fibers by Self-Assembly at an Aqueous Solution Interface," 2002 Textile Res. J., vol. 72, No. 2 (pp. 120-124).
(Continued)

*Primary Examiner* — Kathleen Holwerda
*Assistant Examiner* — Socrates L Boutsikaris
(74) *Attorney, Agent, or Firm* — Harris Beach PLLC

(57) ABSTRACT

A fluid-swellable fiber in particular for the use as a surgical suture, the fiber comprising chitosan, the fiber's swelling ratio being less than 100%, and a fabric comprising the fiber. Moreover, a method of manufacturing from a chitosan-containing solution a fiber comprising chitosan, wherein during manufacture, the solution is brought into contact with a coagulation medium containing at least one organic solvent, a method of removing a fiber from a living organism, wherein the fiber is at least partly dissolved in a solvent applied from the outside, and a kit comprising a chitosan containing fiber and a solvent for at least partly dissolving the fiber.

13 Claims, 2 Drawing Sheets

(56) References Cited

OTHER PUBLICATIONS

Notin, L. et al., "Pseudo-dry-spinning of chitosan," 2006 Acta Biomaterialia vol. 2 (pp. 297-311).
Bini, T.B. et al., "Development of fibrous biodegradable polymer conduits for guided nerve regeneration," 2005 Journal of Materials Science: Materials in Medicine, vol. 16 (pp. 367-375).
Lee, S-H et al., "Fiber Formation and Physical Properties of Chitosan Fiber Crosslinked by Epichlorohydrin in a Wet Spinning System: The Effect of the Concentration of the Crosslinking Agent Epichlorohydrin," 2004 Journal of Applied Polymer Science, vol. 92 (pp. 2054-2062).
Choi, C.Y. et al., "Effect of N-acylation on structure and properties of chitosan fibers," 2007 Carbohydrate Polymers, vol. 68 (pp. 122-127).
Sogias, I.A. et al., "Exploring the Factors Affecting the Solubility of Chitosan in Water," 2010 Macromol. Chem. Phys., vol. 211 (pp. 426-433).

\* cited by examiner

CHITOSAN FIBER

CROSS-REFERENCE TO RELATED APPLICATIONS

This application is a national stage application under 35 U.S.C. §371 of PCT Application No. PCT/EP2010/051231, filed Feb. 2, 2010.

FIELD OF THE INVENTION

The invention relates to a fluid-swellable fiber comprising chitosan, a use of the fiber and a fabric comprising the fiber. It further relates to a method of manufacturing a fiber comprising chitosan, a method of removing a fiber from a patient, and a kit with a fiber comprising chitosan.

BACKGROUND OF THE INVENTION

Chitin and chitosan represent a family of polymers made up of N-acetyl-D-glucosamine and/or D-glucosamine subunits. Chitin can be found widely in the exoskeletons of arthropods, shells of crustaceans, and the cuticles of insects. Chitosan, although occurring in some fungi, is produced industrially by alkaline hydrolysis of chitin. At degrees of acetylation between 0% and about 60%, the upper limit depending on parameters such as processing conditions, molecular weight, and solvent characteristics, the polymer is soluble in dilute acids at a pH of above 6.3. Oftentimes the soluble form of the polymer is referred to as chitosan while for the insoluble form the term chitin is used.

Both chitosan and chitin are promising polymers for a variety of applications. Of these, biomedical applications are of particular interest because of the high biocompatibility of the two polymers, their biodegradability and their structural similarity to the glycosaminoglycans. For comprehensive reviews of potential applications of chitin and chitosan see, for example, Shigemasa and Minami, "Applications of chitin and chitosan for biomaterials", Biotech Genetic Eng Rev 1996; 13, 383-420; Kumar, "A review of chitosan applications", React. Funct. Polym. 2000, 46 (1), 1; and Singh and Ray, "Biomedical applications of chitin, chitosan and their derivatives", J. Macromol. Sci. 2000, C40(1), 69.

Due to its excellent biocompatibility, chitosan has been suggested as a suitable candidate for bioabsorbable surgical sutures. The French patent application FR 2,736,552 to Houbard et al. teaches, for example, the prolongation of the bioresorption time of chitosan implants, including surgical sutures, by acetylation and de-acetylation reactions.

Typically, chitosan fibers are produced by wet-spinning techniques involving the steps of dissolving chitosan in dilute acetic acid and extruding the solution into an alkaline coagulation bath that optionally contains salts such as sodium sulfate. As an alternative method, Notin et al. in "Pseudo-dry-spinning of chitosan", Acta Biomater. 2006, 2, 297, with reference to the international patent application WO/2005025520 describe a pseudo-dry-spinning process to produce chitosan fibers for biomedical applications, such as sutures. For comprehensive reviews on the manufacture of chitosan fibers see, for example, Rathke and Hudson, "Review of Chitin and Chitosan as Fiber and Film Formers", J. Mater. Sci. 1994, C34, 375; Agboh and Qin, "Chitin and chitosan fibers", Polym. Adv. Tech 1996, 8, 355; and Pillai et al., "Chitin and chitosan polymers: Chemistry, solubility and fiber formation", Prog. Polym. Sci. 2009, 34, 641.

Fiber diameters of 0.05 millimeters (mm) or larger can be considered sufficient for the manufacture of surgical monofilament sutures, as defined by the European Pharmacopoeia 4, "Sutures, sterile synthetic absorbable monofilament", ref. 01/2002:0666. The majority of work on chitosan fibers, however, has been focused on the wet-spinning production of chitosan staple fibers using multi-hole spinnerets. The diameter of individual chitosan filaments made by this method is typically well below 0.05 mm.

The production of chitosan monofilaments having diameters equal to or larger than 0.05 mm has been described, for example, in the above-mentioned paper by Notin et al. Using a 0.8 mm needle 2 of 22 mm length, a solution of chitosan in diluted acetic acid (or hydrochloric acid) was extruded into an ammonia atmosphere, resulting in fibers of up to 0.06 mm in diameter. While dry fibers showed a good tensile strength of up to 200 megapascal (MPa), they also exhibited remarkable swelling to between 215% and 400% of the original diameter (which corresponds to about between 450% and 1500% of the original mass) upon contact with physiological saline solution.

In "Production and characterization of chitosan fibers and 3D fiber mesh scaffolds for tissue engineering applications", Macromol, Biosci., 2004, 4, 811, Tuzlakoglu et al. describe the manufacture of a chitosan monofilament of 0.20 mm diameter using a standard wet-spinning procedure. A solution of chitosan in aqueous acetic acid, containing minor amounts of methanol and glycerol, was extruded into a coagulation bath containing a solution of sodium hydroxide and sodium sulphate in distilled water. Dry fibers showed a good tensile strength of 205 MPa; however, fiber mass due to swelling reached 210% of the dry fiber after immersion in saline solution.

In "Coagulation rate studies of spinnable chitosan fibers", J. Polym. Sci. A 1999, 37B, 1079, Knaul et al. have proposed a method of decreasing the swelling of chitosan fibers by applying a cross-linking reaction using glyoxal or glutaraldehyde. On the example of chitosan filaments with a diameter of 22 micrometers (μm) it was found that by using large amounts of cross-linking agent swelling could be reduced to about 135% to 150% of the original diameter (corresponding to about 180% to 220% of the original mass).

Problem to be Solved by the Invention

It is an objective of the present invention to provide an improved fluid-swellable fiber comprising chitosan, a use of the fiber and a new fabric comprising the fiber. It further aims to provide an improved method of manufacturing a fiber comprising chitosan, an improved method of removing a fiber from a patient and a new kit comprising a fiber which fiber contains chitosan.

Solution According to the Invention

According to the invention, the problem is solved by a fluid-swellable fiber comprising chitosan, the fibers' swelling ratio being less than 100%. Moreover, the problem is solved by the use of the fiber as a surgical suture thread, and by a fabric comprising the fiber or several of the fibers.

The problem is also solved by a method of manufacturing from a chitosan-containing solution a fiber comprising chitosan, wherein during manufacture the solution is brought into contact with a coagulation medium containing at least one organic solvent. Further, the problem is solved by a method of removing a fiber from a living organism, e.g. human, wherein the fiber is at least partially dissolved in a solvent applied from the outside. Finally, the problem according to the invention is solved by a kit comprising a containing-chitosan fiber and a removal solvent for at least partly dissolving the fiber.

In the following, the term "chitosan", this is meant to encompasses all poly(N-acyl-D-glucosamine-D-glucosamine)copolymers as well as poly(D-glucosamine)homopolymers and poly(N-acyl-D-glucosamine)homopolymers and its derivatives. Thus, it includes both soluble and insoluble forms of the polymer and is not limited to certain degrees of acylation. Moreover, it includes both "native chitosan" and any "chitosan derivative", cross-linked and/or otherwise modified. The term "native chitosan" in the context of the present invention refers to poly(N-acetyl-D-glucosamine-D-glucosamine)copolymers, poly(D-glucosamine)homopolymer and poly(N-acetyl-D-glucosamine) homopolymers. "Native chitosan" includes both the native chitosan base and native chitosan in the form of a chitosan salt. Conversely, any cross-linked or otherwise chemically modified chitosan is referred to as "chitosan derivative", having different properties than native chitosan.

The expression "fluid-swellable" in the context of the present invention refers to the fiber's property to take up an aqueous medium upon contact with the aqueous medium, thereby increasing the fiber's overall mass. The "swelling ratio" is calculated according to the formula:

$$(m_w - m_d)/m_d \times 100\%,$$

wherein $m_d$ is the mass of the dry fiber before contact with an aqueous solution and $m_w$ is the mass of the fiber after saturation with a physiological solution, such as a saline or a buffered solution at neutral pH.

The terms "dissolvable" and "dissolution" in the context of the present invention refer to a process of mass loss of a solid form of the chitosan without molecular weight decrease (i.e. without decrease in polymer chain length) due to solubility in an aqueous environment. This is to be distinguished from "degradation", which is the process of molecular weight decrease due to depolymerisation of chitosan.

The term "suture" as used in the context of the present invention refers to a wound-closure device that can serve to approximate tissue of a living organism, e.g. a human, during wound healing.

Advantageously, when used as a suture, the moderate swelling of the fiber can support the stitch channels and close them to prevent bleeding, e.g. in vascular anastomosis applications. Yet, advantageously, the swelling of the fiber according to the invention is still small enough to ensure sufficient mechanical strength even when swollen. This is in contrast to some prior art materials which may lose strength considerably due to excessive swelling. Moreover, advantageously, with the fiber according to the invention unwanted tissue compression, which can also be a result of excessive swelling, can be avoided.

In some embodiments, the present invention exploits the solubility of chitosan to attain an at least partially soluble fiber. At least partial dissolution of the fiber can facilitate its removal, e.g. when it is used as a suture thread. It can even be achieved with the invention that the fiber is completely dissolvable. Dissolvability of the fiber supports the removal of a chitosan suture that is either absorbable or non-absorbable, in the sense of the definition in the European Pharmacopoeia 4, Ref. 01/2002:0666 or the European Pharmacopoeia 5, Ref. 01/2005:0660. The suture material can be produced, sterilized, tested, packaged and labeled as required in the above documents.

Advantageously, due to chitosan's high biocompatibility, a highly biocompatible fiber can be achieved with the invention and tissue irritation caused by the fiber can be avoided when used in a living organism, e.g. as a suture material. Moreover, advantageously, the antibacterial properties of chitosan can be exploited to suppress an accumulation of bacteria on the fiber, e.g. when used as a suture. It is another achievable advantage of the invention that the property of chitosan to promote wound healing can be exploited to obtain a fiber that improves wound healing, in particular when used as a suture material.

PREFERRED EMBODIMENTS OF THE INVENTION

Preferred features of the invention which may be applied alone or in combination are discussed in the dependent claims and in the following description.

A preferred fiber has a swelling ratio of 100% or less, more preferably 80% or less. The fiber's preferred swelling ratio is more than 10%, preferably more than 30%, preferably more than 50%, e.g. between 60 and 70%.

Preferably, the fiber comprises a chitosan component dissolvable in an aqueous medium, the solubility depending on the overall pH. Preferably, this is the only chitosan component of the fiber. Due to the pH-dependent solubility, disintegration can be controlled by means of controlling the pH. In particular, the fiber can serve at a first pH to approximate the tissue during the healing period. Subsequently, at a second pH the fiber can be dissolved to remove it, at least partially. Some embodiments of the invention exploit the fact that a wound's exudative fluid can have a pH high enough to prevent dissolution. When the pH is lowered by external intervention, e.g. by applying an acidic—preferably mildly acidic—liquid, dissolution can be invoked.

A preferred fiber according to the invention has a diameter of 0.05 mm or more. Fiber diameters of 0.05 mm or larger in general are considered sufficient for the manufacture of surgical monofilament sutures. As described further below, monofilament sutures have certain advantages over multifilament sutures. With fiber diameters of 0.05 mm or larger it is achievable that such sutures have sufficient initial strength. Diameters are measured according to the method described in the European Pharmacopoeia 4, "Sutures, sterile synthetic absorbable monofilament", Ref. 01/2002:0666. The preferred diameter of the fiber is equal or greater than 0.07 mm, preferably equal or greater than 0.1 mm, more preferably equal or greater than 0.15 mm. The preferable diameter is smaller than 1 mm, more preferably smaller than 0.5 mm.

In one embodiment of the invention, the fiber comprises a chitosan component that has a degree of acylation, preferably acetylation, of 40% or less, preferably 20% or less, preferably 10% or less. Preferably, this is the only chitosan component of the fiber. Advantageously, such rather low degrees of ac(et)ylation can result in high mechanical strength of the chitosan material and thus the fiber. Preferably, this chitosan component is dissolvable in an aqueous medium, the solubility depending on the pH.

In one embodiment of the invention, the fiber comprises a chitosan component that has a degree of acetylation of 60% or more, preferably 80% or more, preferably 90% or more. Preferably, this is the only chitosan component of the fiber. Advantageously, with such rather high degrees of acetylation, a reasonable strength of the fiber can be achieved while at the same time providing for a good biodegradability.

The preferred fiber comprises non-cross-linked chitosan as a component, more preferably, as the only chitosan component. It is an achievable advantage of non-cross-linked chitosan that a blockage of active functionalities of chitosan, which is often the result of cross-linking, be it ionically or covalently, can be avoided. In particular, blockage of the amine groups, which can significantly reduce biocompatibility, dissolvability, and biodegradability, can be avoided. Moreover, problems arising from the toxic nature of some cross-linking agents can be avoided. Preferably, the fiber comprises a native chitosan as a component, preferably as the only chitosan component. In this embodiment, advantageously, the high biocompatibility, non-toxicity, and bacteriostatic properties of native chitosan can be exploited.

The fiber according to the invention may consist entirely of chitosan or it may consist of a combination of chitosan with other materials, e.g. at least one other polymer. Nevertheless, preferably chitosan makes up more than 50% by weight, more preferably more than 90% by weight, of the fiber. Suitable polymers include those from the group of synthetic polyesters, such as homopolymers and copolymers based on glycolide, L-lactide, D,L-lactide, p-dioxanone, ε-caprolactone; natural polyesters, such as those from the group of the polyhydroxyalkanoates, such as homopolymers and copolymers based on 3-hydroxybutyrate, 4-hydroxybutyrate, 3-hydroxyvalerate, 3-hydroxyhexanoate, 3-hydroxyoctanoate; polyorthoesters; polycarbonates; polyanhydrides; polyurethanes; polyphosphazenes; polyphosphoesters; polysaccharides; polypeptides; silk; cotton; homopolymers or copolymers based on vinyl alcohol, vinyl acetate, N-vinyl pyrrolidone, ethylene glycol, propylene glycol; polypropylene, polyamide, polytetrafluoroethylene, polyethylene terephthalate, polybutylene terephthalate, as well as derivatives, copolymers, and blends based on the abovementioned polymers. Additionally or alternatively, other substances can be incorporated into the fiber. The fiber may for example comprise at least one pharmaceutically active and/or bioactive additional component. Suitable bioactive additional components may e.g. be proteins, peptides or derivatives thereof, nucleic acids or derivatives thereof, low molecular weight compounds active as drugs, such as antibiotics or anti-inflammatory drugs, or agonists or antagonists of the innate immune system, immunomodulators, -inhibitors or -agonists, or stimulating or differentiating growth factors for stimulating or differentiating growth of at least one subtype of cells. Alternatively or in addition, the fiber may contain one or more plasticizers, e.g. glycerol, or one or more dyes, e.g. indigocarmine. The plasticizer may also be chosen from the above list of suitable polymers that may be added to the chitosan fiber. By adding a dye, the filament can be colored, thereby facilitating handling of the fiber, e.g. when used as a suture. Another suitable additive may be particles of a contrast agent, or micro- or nanoparticles that may contain bioactive components. Despite the presence of other components in the fiber, the chitosan preferably is the fiber's main component.

When the fiber according to the invention is used as a suture thread, it is preferably used as a single fiber, also referred to as a monofilament. A single fiber suture can be easier to knot which may prove advantageous in particular during placement of the suture. Also, advantageously, bacteria are less prone to accumulate on a monofilament. Nevertheless, the present invention also encompasses suture threads that comprise of several fibers spun into a multifilament thread, such as staple fibers. The fibers according to the invention may also be processed into a fabric, e.g. a woven, a knitted, or a crocheted fabric. Such fabrics may e.g. be suitable as implants or as part of implants such as stent covers.

In the method according to the invention of manufacturing a fiber from a chitosan-containing solution, the coagulation medium with which the solution is brought into contact preferably is a fluid medium. Suitable solvents include organic liquids, such as methanol, ethanol, propanol, butanol, trifluoroethanol, ethylene glycol, diethylene glycol, polyethylene glycol, glycerol, formamide, N,N-dimethyl formamide, N-methylpyrrolidone, dimethyl sulfoxide, dioxane, and tetrahydrofurane. Preferably, in addition to the organic solvent, the coagulation medium comprises further components, e.g. ammonia, which may be present in the form of an ammonia solution, or another substance that is suitable to promote coagulation. Yet the preferred coagulation medium comprises at least 50%, more preferably at least 70%, more preferably at least 90%, more preferably at least 98% by weight of the organic solvent or solvents.

Preferably, the solution is extruded into the coagulation medium, preferably into a bath of the coagulation medium. For this purpose, a needle may be used that is dipped into the coagulation bath. The chitosan-containing solution can be extruded under pressure through the needle into the coagulation bath. The skilled person will adjust the needle diameter and the pressure to obtain the desired fiber diameter and an appropriate manufacturing speed.

After extrusion, the fiber preferably is left in the coagulation bath long enough to ensure that coagulation is essentially completed. This may require for example 4 or 8 hours. After coagulation, the fiber is preferably washed once, twice, or more often to remove the organic solvent. A typical washing medium is a diluted aqueous solution of ammonia, e.g. a 0.025% ammonia solution.

In at least one of the washing steps, preferably in the last washing step, the washing medium may contain a plasticizer, e.g. glycerol. Typically the glycerol is present in the washing medium at a concentration of more than 0.1% by weight, preferably more than 0.5% by weight. In at least one of the washing steps, preferably the last washing step, the washing medium may contain a dye, e.g. indigocarmine. Typically the stain is present in the washing medium at a concentration of less than 0.1% by weight, preferably less than 0.05% by weight. The typical washing step takes between 0.5 and 4 hours, e.g. between 1 and 3 hours.

In one embodiment of the invention, the fiber is dried once washing has been completed. Typically, each section of the fiber is dried for at least one minute (min), preferably for at least 5 min. Drying preferably takes place in a continuous process in which the fiber runs through a drying path. At the end of the drying path, the fiber may be wound up.

Preferably, the solution from which the fiber is extruded contains at least one organic solvent, such as methanol, ethanol, propanol, butanol, trifluoroethanol, ethylene glycol, diethylene glycol, polyethylene glycol, glycerol, formamide, N,N-dimethyl formamide, N-methylpyrrolidone, dimethyl sulfoxide, dioxane, and tetrahydrofurane. Preferably the solvent is present in the solution in a concentration low enough to ensure that the chitosan does not yet coagulate. Advantageously, by providing the organic solvent already in the solution from which the fiber is extruded, coagulation upon contact with the coagulation medium can be accelerated. In particular the manufacture of fibers with greater diameters can be facilitated.

A preferred method of manufacturing a fiber according to the invention comprises an acylation step in which the chitosan in the fiber is acylated, preferably acetylated. In some embodiments of the invention, in the acylation step the fiber is brought into contact with an acylation medium, which medium preferably is present as an acylation bath, in which the fiber can be immersed for acylation. The acylation medium may e.g. contain acetic anhydride as an acylation agent. In addition to the acylation agent, a preferred acylation medium contains water. This, advantageously, can help to increase swellability of the fiber, thereby facilitating penetration of the rection mixture into the fiber material. Thus, the acylation medium preferably is dissolved in water. The preferred acylation medium contains an organic solvent, e.g. methanol, ethanol, propanol, butanol, trifluoroethanol, ethylene glycol, diethylene glycol, polyethylene glycol, glycerol, formamide, N,N-dimethyl formamide, N-methylpyrrolidone, dimethyl sulfoxide, dioxane, and tetrahydrofurane. Advantageously, the presence of an organic solvent can help to decrease the polarity of the acylation medium, thereby facilitating covalent acylation reactions.

The method according to the invention may comprise a hydrolysis step in order to reduce the degree of acylation. The hydrolysis medium may e.g. be an aqueous sodium hydroxide solution, in which the fiber is stored preferably at an elevated temperature, e.g. 100° C., for several hours.

In the method of removing a fiber from a living organism, in particular a patient, (at least one of) the chitosan component(s) of the fiber is dissolved. The solvent applied preferably is an aqueous solvent. It may e.g. be an aqueous solution of ionic compounds, such as an aqueous sodium chloride solution, a buffered solution, such as an acetic acid/acetate buffered solution, or an aqueous solution of non-ionic compounds, such as an aqueous glucose solution. For dissolving the fiber, the solvent to be applied on the fiber may be applied directly, or alternatively incorporated in a gel, e.g. gelatin gel, or soaked in a tissue, e.g. gauze, band-aid, etc. The preferred pH of the solvent is acidic, preferably mildly acidic. Thereby it can be exploited that chitosan dissolves in such solvents. Preferably, the medium's pH is below 6.3, more preferably below 6. The preferred pH of the aqueous medium is preferably above 3.5, more preferably above 4, more preferably above 4.5.

The preferred kit according to the invention contains a suture material containing chitosan and a solvent for at least partly dissolving the suture material. Preferably the fiber is a fiber as described above. Moreover, a preferred kit according to the invention comprises a removal solvent for at least partly dissolving the fiber to remove the fiber at least partly from the living organism, e.g. a human. The amount of removal solvent provided in the kit is at least five times per weight the amount of chitosan provided in the kits' fiber. The removal solvent is packaged separated from the fiber, for example, in a sealed bottle or a disposable pipette, in a gauze, a sponge, or gel. In some embodiments of the invention, the solvent is provided in a spray bottle or spray can for easy application.

BRIEF DESCRIPTION OF THE DRAWING

The invention is illustrated in greater detail with the aid of a schematic drawing.

DETAILED DESCRIPTION OF EXEMPLARY EMBODIMENTS OF THE INVENTION

Example 1

Figure 1:
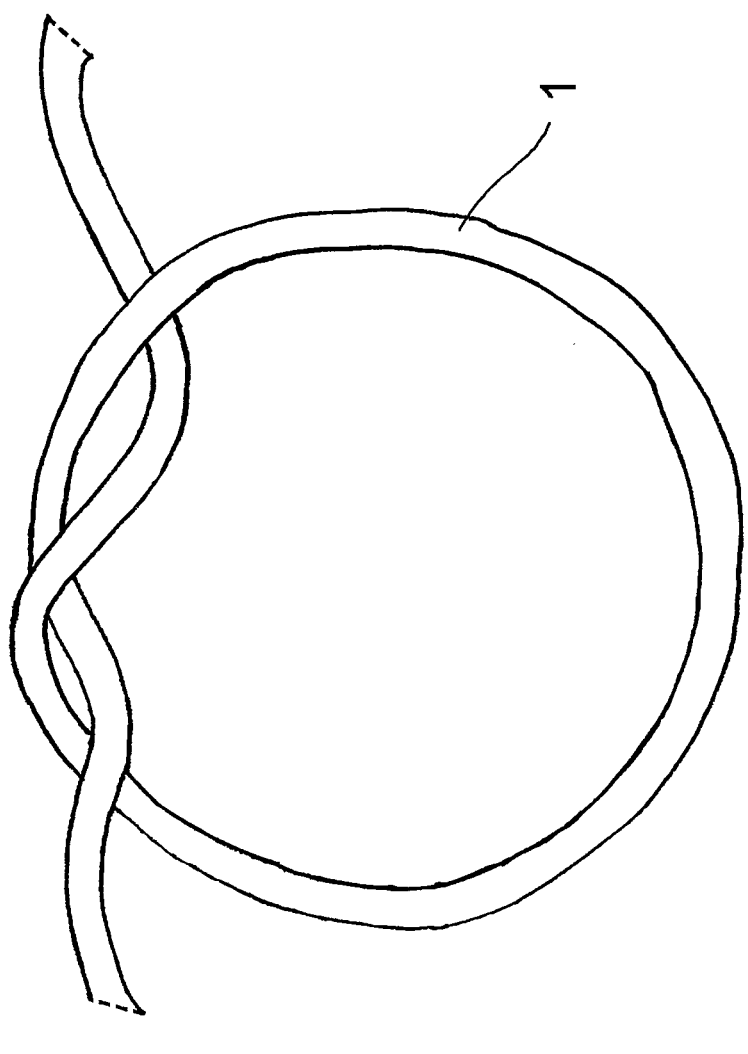
FIG. 1 shows a fiber according to the invention formed into a simple knot. Not drawn to scale.

Fabrication of Chitosan Monofilament 50 ml of a solution of 4% chitosan in 2% acetic acid were mixed with an equal amount of N-methylpyrrolidone (NMP) and filled in a 0.1 liter (L) glass container equipped with a cap containing 2 outlets. One outlet is connected to an air compressor, and the other outlet connects the chitosan solution to a needle of 50 mm in length and an inner diameter of 1.0 mm. The needle is dipped into a coagulation bath containing a mixture of 2 L of NMP and 3 milliliters of 25% aqueous ammonia solution. The air pressure is adjusted to 490 millibar±20 millibar, to extrude the chitosan solution into the coagulation bath.

After completion of the extrusion, the fiber is left in the coagulation bath over night. It is then washed in a mixture of distilled water containing 0.1% by weight of a 25% aqueous ammonia solution for 2 hours. For a second washing step, the solution is replaced by a mixture of distilled water containing 0.1% by weight of a 25% by weight aqueous ammonia solution and 1% by weight of glycerol as plasticizer to wash the fiber for another 2 hours. In some experiments, 0.01% by weight of indigocarmine was added to this mixture for blue staining. After the washing steps, the fiber is removed from the bath, and dried at room temperature while being wound up at a speed of 1 meters/min.

Monofilaments 1 (schematically shown in FIG. 1) of several hundred meters length were obtained by this method. Moreover, short-length monofilaments (as sufficient for sutures) were obtained by winding up the monofilament 1 directly on metallic holders being 50 centimeters (cm) apart from each other for drying at room temperature over night. The chitosan monofilament 1 resulting this way had a diameter of approximately 0.17 mm.

Chitosan monofilaments 1 of different diameters were produced by using needles of different inner diameters.

Example 2

Acetylation of Chitosan Monofilament 29.3 g of chitosan monofilaments 1 manufactured as described in Example 1, except of the drying step, were treated with 1 L of a 0.01% by weight solution of acetic anhydride in a mixture of NMP/water at a ratio of 60/40 by volume for 2 hours under gentle shaking, and then washed and dried as described in Example 1, resulting in an N-acetylchitosan monofilament.

Fabrication of Chitosan Suture

Figure 2:
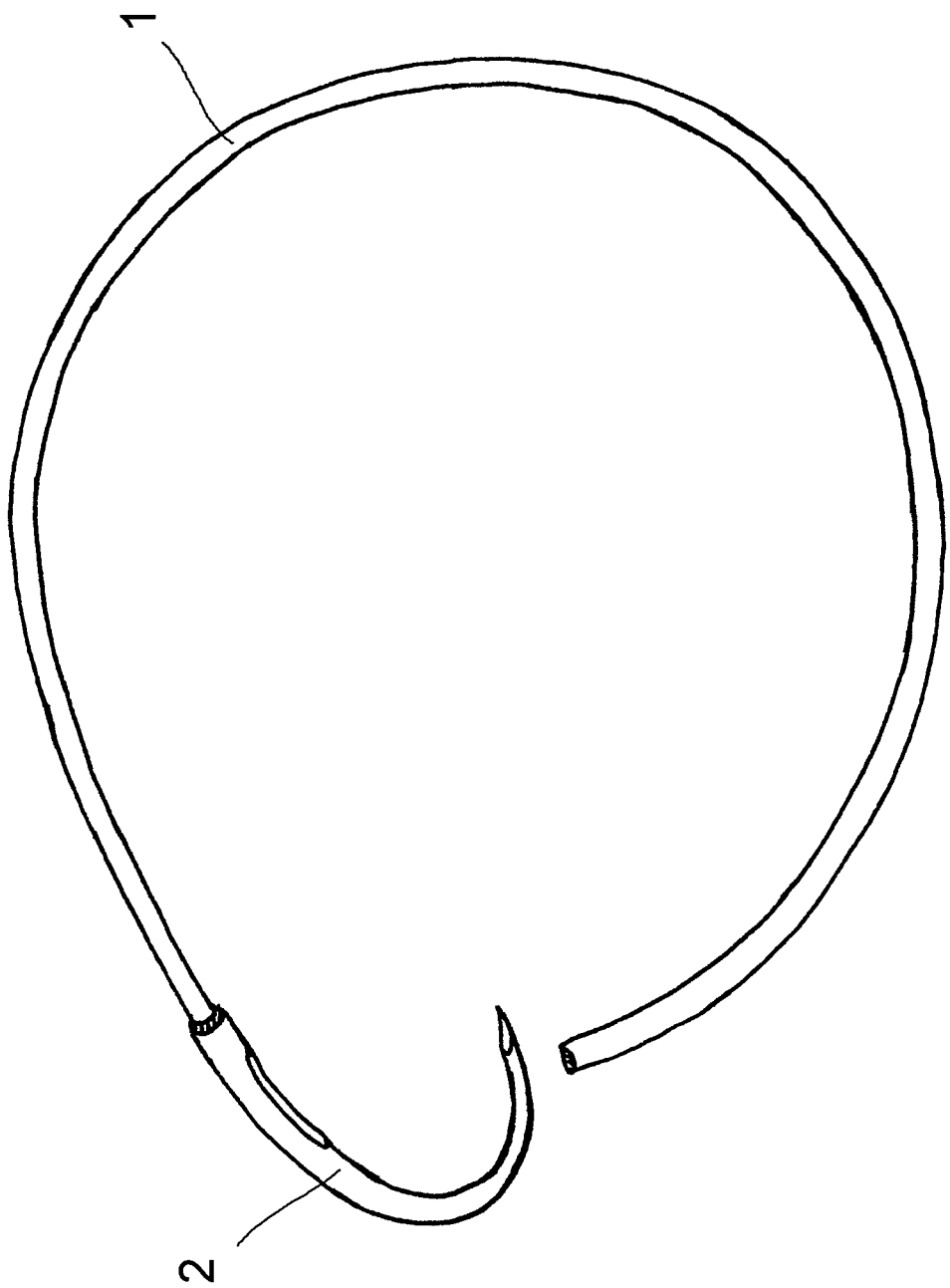
FIG. 2 shows a suture material according to the invention. Nat drawn to scale.

Monofilaments 1 fabricated as described in Examples 1 and 2 (dried on holders) were cut to a length of 45 cm, and needles 2 of the type DS 19 (for 0.17 mm monofilaments 1) and DS 30 (for 0.34 mm monofilaments 1) were attached, using standardized procedures, by Feuerstein GmbH (Berlin, Germany). An example of a chitosan suture is shown in FIG. 2.

Swellability

Chitosan monofilaments 1 and sutures produced as described in Examples 1 to 3, were weighted, and then placed in a 0.9% aqueous NaCl solution of pH 7.0 for 1 hour. The mass of the wet monofilament 1 was compared to the mass of the dry monofilament 1, and the swelling ratio calculated. Examples are given in Table 1.

TABLE 1

| No. | Sample | Diameter (mm) | Swelling ratio (%) |
|---|---|---|---|
| 1 | chitosan | 0.05 | 42 |
| 2 | chitosan | 0.08 | 47 |
| 3 | chitosan | 0.17 | 65 |
| 4 | chitosan | 0.34 | 63 |
| 5 | chitosan | 0.44 | 76 |
| 6 | N-acetylchitosan | 0.34 | 97 |

Mechanical Properties

Mechanical strength of chitosan and N-acetylchitosan monofilaments 1 and sutures produced as described in Examples 1 to 3 were tested according to the procedure specified in the European Pharmacopoeia 4, ref. 01/2002: 0666. Knots 2 as shown in FIG. 1 where formed and knot strengths were measured. Examples for knot strengths are given in Table 2.

TABLE 2

| No. | Sample | Diameter (mm) | Breaking load (N) |
|---|---|---|---|
| 3 | chitosan | 0.17 | 5.7 |
| 4 | chitosan | 0.34 | 16.9 |
| 6 | N-acetylchitosan | 0.34 | 7.0 |

Needle Attachment

Needle 2 attachment of chitosan and N-acetylchitosan sutures produced as described in Examples 1 and 2 were tested according to the procedure specified in the European Pharmacopoeia 4, ref. 01/2002:0666. Examples for needle 2 attachment strengths are given in Table 3.

TABLE 3

| No. | Sample | Diameter (mm) | Breaking load (N) |
|---|---|---|---|
| 3 | chitosan | 0.17 | 6.5 |
| 4 | chitosan | 0.34 | 11.1 |
| 6 | N-acetylchitosan | 0.34 | 13.3 |

Biocompatibility

Chitosan suture (0.24 mm diameter) was fabricated as described in Example 3 and sterilized using an electron beam. 10 NMRI mice were anesthetized, and a 1.5 cm long piece of the suture implanted subcutaneously in the neck of each animal. The neck incision was closed by a conventional, non-absorbable suture. No infection or immunogenic reaction was observed in the macroscopic follow-up. After 4, 8, and 12 weeks, the chitosan samples were explanted, and the area of implantation was analyzed histologically. None of the tissue samples showed signs of inflammation or other changes. After 4 weeks, blood samples were taken and controlled for chronic inflammation, by analysis of the number of leukocytes. It was found that in all animals the number of leukocytes was in the normal range indicating no inflammatory reaction to the chitosan material.

Biodegradation

Samples of chitosan suture, obtained from the implantation study described in Example 7, were tested for tensile strength 4, 8, and 12 weeks post-implantation. Breaking loads were found to decrease to 41, 26, and 11%, respectively.

Controlled Dissolution

Chitosan suture of 0.24 mm in diameter was fabricated as described in Example 3 and sterilized using electron beam. 6 NMRI mice were anesthetized, and the suture, using 3 stitches each, applied to the neck of each animal. One week post-implantation, a gelatin gel, adjusted to pH 5 using diluted acetic acid, was applied externally to the implant area of three of the animals. Essentially complete dissolution of the accessible suture material was observed within 4 hours of gel application. The remaining three animals were treated the same way 4 weeks post-implantation, leading to similar results.

The features described in the above description, claims and figures can be relevant to the invention in any combination. The reference numerals in the claims have merely been introduced to facilitate reading of the claims and are by no means meant to be limiting.

The invention claimed is:

1. A fluid-swellable fiber comprising more than 90% by weight of chitosan, wherein:
   the diameter of the fiber is at least 0.05 millimeters,
   the fiber's swelling ratio is 80% or less, and
   the swelling ratio defines a change in mass calculated according to formula:

$(m_w - m_d)/m_d \times 100\%$, wherein:
   $m_d$ is the mass of the dry fiber before contact with an aqueous solution, and
   $m_w$ is the mass of the fiber after saturation with a physiological solution.

2. The fiber of claim 1, wherein the fiber's swelling ratio is between 60% and 70%.

3. The fiber of claim 1, wherein the fiber's swelling ratio is more than 10%.

4. The fiber of claim 1, comprising a chitosan component that is dissolvable in an aqueous medium, the solubility of the chitosan component depending on the pH.

5. The fiber of claim 1, comprising a chitosan component that has a degree of acetylation of more than 60% or less than 40%.

6. The fiber of claim 1, comprising non-cross-linked chitosan.

7. The fiber of claim 1, comprising a native chitosan.

8. The fiber of claim 1, comprising a combination of chitosan and at least one other polymer.

9. A process for carrying out surgical suturing comprising:
   using a fluid-swellable fiber comprising chitosan as a surgical suture, wherein:
   the fiber comprises more than 90% by weight of chitosan,
   the diameter of the fiber is at least 0.05 millimeters,
   the fiber's swelling ratio is 80% or less, and
   the swelling ratio defines a change in mass calculated according to formula:

$(m_w - m_d)/m_d \times 100\%$, wherein:
   $m_d$ is the mass of the dry fiber before contact with an aqueous solution, and
   $m_w$ is the mass of the fiber after saturation with a physiological solution.

10. A fabric comprising at least one fiber of claim 1.

11. A method for manufacturing, from a chitosan-comprising solution, a fluid-swellable fiber comprising chitosan, wherein:
   the fluid-swellable fiber comprises more than 90% by weight of chitosan,
   the diameter of the fluid-swellable fiber is at least 0.05 mm, the swelling ratio of the fluid-swellable fiber is 80% or less, the swelling ratio defines a change in mass calculated according to formula:

$$(m_w - m_d)/m_d \times 100\%,$$

wherein:

$m_d$ is the mass of the dry fiber before contact with an aqueous solution, and $m_w$ is the mass of the fiber after saturation with a physiological solution, the method comprising:

bringing the chitosan-comprising solution into contact with a coagulation medium, wherein the coagulation medium comprises at least one organic solvent.

12. The method of claim 11, wherein the coagulation medium comprises at least 50% of the at least one organic solvent.

13. The method of claim 11, comprising the step of acylating the chitosan in the fluid-swellable fiber.

* * * * *